United States Patent [19]

Tang

[11] Patent Number: 4,569,351
[45] Date of Patent: Feb. 11, 1986

[54] APPARATUS AND METHOD FOR STIMULATING MICTURITION AND CERTAIN MUSCLES IN PARAPLEGIC MAMMALS

[75] Inventor: Pei C. Tang, Glen Ellyn, Ill.

[73] Assignee: University of Health Sciences/The Chicago Medical School, Chicago, Ill.

[21] Appl. No.: 684,351

[22] Filed: Dec. 20, 1984

[51] Int. Cl.$^4$ .............................................. A61N 1/36
[52] U.S. Cl. ................................. 128/419 E; 128/784
[58] Field of Search ............... 128/419 E, 419 R, 421, 128/642, 783–785

[56] References Cited

U.S. PATENT DOCUMENTS

| | | | |
|---|---|---|---|
| 3,357,434 | 12/1967 | Abell | 128/419 E |
| 3,646,940 | 3/1972 | Timm et al. | 128/419 E |
| 3,650,276 | 3/1972 | Burghele et al. | 128/419 E |
| 3,667,477 | 6/1972 | Susset et al. | 128/419 E |
| 3,870,051 | 3/1975 | Brindley | 128/419 E |

FOREIGN PATENT DOCUMENTS 1434524  5/1976  United Kingdom ................ 128/421

OTHER PUBLICATIONS

Naumann et al., "A Sequential Stimulator for Electrical Restoration of the Micturition Reflex", IEEE Trans. Biomed. Eng., vol. BME-25, No. 3, May 1978, pp. 307–311.
Timm et al., "Electromechanical Restoration of the Micturition Reflex", IEEE Trans. Biomed. Eng., vol. BME-18, No. 4, Jul. 1971, pp. 274–280.
Schamaum et al., "Management of Neurogenic Urinary Bladder in Paraplegic Dogs by Direct Electronic Stimulation of the Detrusor", Surgery, Oct. 1963, vol. 54, No. 4, pp. 640–649.

Primary Examiner—William E. Kamm
Assistant Examiner—Mitchell J. Shein
Attorney, Agent, or Firm—Norman Lettvin

[57] ABSTRACT

There is disclosed a new, useful and simple apparatus, and surgical method, for implantation of same, for selective control of evacuating the urinary bladder in mammals by electrical stimulation of the motor innervations of the bladder's detrusor urinae muscle. Contractions of this muscle occur by timed electrical pulses conducted by electrodes placed in the fluid of the sacral canal, to conduct electrical stimulus through the fluid in the sacral region of the spinal cord. Nerve roots located in this region of the sacral canal, and which innervate the bladder, are stimulated by the electricity conducted by the fluid, causing contraction of the bladder's detrusor muscle, and results in micturition. In preferred form, the apparatus may be used on paraplegic or quadriplegic humans and could be selectively controllable by a paraplegic human. The apparatus may also be used to evacuate the bladder in paraplegic mammals such as dogs and cats. The apparatus can be used to stimulate nerves innervating muscles other than the detrusor in the body, and thereby to exercise the muscles that are paralyzed by a spinal cord injury.

9 Claims, 4 Drawing Figures

APPARATUS AND METHOD FOR STIMULATING MICTURITION AND CERTAIN MUSCLES IN PARAPLEGIC MAMMALS

FIELD OF THE INVENTION

This invention relates to apparatus and method of effecting and controlling micturition, and also to effect stimulation of certain muscles to slow deterioration thereof, by and in mammalian animals, including humans, that have suffered a condition, or injury, causing the animal or human to be at least paraplegic.

BACKGROUND OF THE INVENTION

Rentention of urine in the bladder is a serious problem in paraplegic and quadraplegic mammals, such as dogs and humans. It results from a failure to empty the bladder due to an interruption of the spinal pathway from the pontine micturition center in the brain to the bladder. Eventually such a condition will induce urinary tract infection and renal complications that often lead to, or cause, premature death. Prior attempts have been made to induce micturition in humans, and in test mammalian animals by electrical stimulation of pre- and post-ganglionic parasympathetic neurons that innervate the bladder. In such prior experimental attempts, the electrical stimulator has been connected directly to, or wrapped around, the nerves that are to be stimulated.

Neurophysiologically, if a specific nerve is to be electrically stimulated, it must be isolated from other excitable tissues. In a traditional experimental method, a pair of stimulating electrodes are directly attached to each nerve root to be stimulated, sometimes with use of an associated isolating protective or insulating device. However, because there is only limited space available in the sacral canal of test mammals, and also of humans, and further because of the difficulty in locating a specific nerve root, it has been observed that prior attempts to arrange electrodes to be operatively associated with only one or two nerve roots functions to restrict stimulation to only a portion of the motor innervations of the bladder of a mammalian test animal.

Heretofore, it was thought to be desirable that the first sacral roots be spared from stimulation to avoid a stimulation that would produce unnecessary movements of the body and the legs. While such thought probably had stimulus in the fact that experimenters were working only with test animals and sought to eliminate unnecessary body and muscle movement of the test animal, the stimulation and movement of muscles is probably desirable to limit deterioration of the musculature, particularly in a human. The first sacral roots may contain motor fibers both to the detrusor muscle, and to other muscles in both animals and humans. In so far as stimulation of the first sacral roots may effect stimulation that causes body and muscle movement in a human, such stimulation is not necessarily to be avoided.

However, prior art methods for stimulating a mammalian animal's bladder to effect discharge therefrom, has employed restricted stimulation in attempts to isolate the electrical stimulation to a particular nerve root, and to avoid spreading the stimulating electricity to other excitable tissues.

Reports of: (a) Agnew, W. F., et al., *The Effects of Electrical Stimulation On The Central And Peripheral Nervous Systems*, NIH Contract, NO-1-NS-0-2275 Quarterly Progress Report, Oct. 1-15, (1979); (b) Brindley, G. S., *An Implant To Empty The Bladder Or Close The Urethra*, J. Neurol. Neurosurg. Psychiat., 40: 358-369, (1977); (c) Schmidt, R. A., et al., *Feasibility of Inducing Micturition Through Chronic Stimulation Of Sacral Roots*, Urology, 12: 471-477, (1978); (d) Tanagho, E. A., et al., *Studies On The Feasibility of Urinary Bladder Evacuation By Direct Spinal Cord Stimulation*, NIH Contract, NO-1-NS-3-2307, Quarterly Progress Report, Apr. 1-14, (1981); all advise that prior investigations have attempted to stimulate motor neurons of the bladder by placing stimulating electrodes as close as possible to the specific nerve to be stimulated, often accompanied by the presence of some insulating device. However, it has been observed that tightly attached electrodes and protective devices obstruct axonal transport, cause leakage of the cerebrospinal fluid, and may irreparably damage the animal's nerve roots.

Brindley, G. S., *An Implant To Empty The Bladder Or Close The Urethra*, J. Neuro. Neurosurgical Psychiatry, 40: 358-369, (1977), designed an implant to stimulate only separate strands of sacral roots in the sacral canal. However, leakage of cerebrospinal fluid, as well as injury to the spinal roots is reported to have occurred with said apparatus.

The general concept of using only intermittent stimulation to induce animal micturition has been previously suggested by others. U. Jonas, and E. A. Tanagho, as reflected in their reports, *Studies On The Feasibility Of Urinary Bladder Evacuation By Direct Spinal Cord Stimulation*, and, *Poststimulus Voiding: A Way To Overcome Outflow Resistance*, Investigative Urology, 13: 151-153, (1975), intermittently stimulated the sacral roots to achieve micturition. However, they achieved micturition only when a four-channel urethral catheter was positioned in the bladder.

Stimulating currents which are non-injurious to the body have been previously explored and reported. P. C. Tang, *pH Changes Induced By Electrical Stimulation*, Physiologist, 22: 122, (1979). It has been observed that monophasic electrical pulses, which are essentially intermittent direct currents, generate gases and cause severe pH changes at the electrode terminals. Alternating currents, such as capacitor-coupled and bi-phasic pulses are generally injurious to the body. The voltage of capacitor-coupled pulses varies with the frequency of the stimulation, while the bi-phasic pulses are difficult to balance and expensive to use.

SUMMARY OF THE INVENTION

A new, useful, and simple apparatus, and surgical method, is provided for effecting controlled micturition in mammals afflicted with paraplegic or quadriplegic injury that adversely affects normal micturition by the subject.

Paraplegic mammals, such as spinal dogs and humans, have difficulty in effecting complete, or substantially complete, emptying of the bladder of urine. Where the spinal cord of a test dog has been severed, such as by transection, the subject is referred to hereinafter as a "spinal" dog.

It has heretofore been known to experiment with control of urine voiding, by paraplegic animals, by electrical stimulation of the pre- and post-ganglionic parasympathetic neurons innervating the bladder. In the conventional method of electrical stimulation seeking to effect voiding of urine in paraplegic animals, a pair of stimulating electrodes are tightly attached to the nerves, often with some protective insulation. However, such tightly attached electrodes and protective devices have been known to obstruct axonal transport and cause irreparable damage to nerves involved.

The improved method of electrical stimulation described hereinafter, also referred to as the "volume conduction" method, appears to be less harmful to the nerve tissue than said conventional method of nerve stimulation.

In the "volume conduction" method of nerve stimulation used in the invention disclosed herein, three stimulating electrodes are employed and are not directly attached to the nerves. Instead, the free ends of three stimulating electrodes are immersed in the fluid medium of the sacral canal of the paraplegic mammal, the fluid medium serving as the volume conductor. The stimulating voltage is preferably between 4–6 volts, although voltage intensity has been used as high as 6–8 V.

Previous studies reflected that monophasic electric pulses, which are intermittent direct currents, generate gases and cause severe pH changes at the electrode terminals when using the volume conduction method. It now appears that a form of stimulating current that is apparently non-injurious includes capacitor-coupled pulses, bi-phasic pulses, and sine wave alternating currents. Because the voltage of capacitor-coupled pulses varies with the frequency of stimulation, and because biphasic pulses are difficult to balance and expensive to use, the use of 60 Hz AC current is preferred in the volume conduction method of nerve stimulation, as it is non-injurious to the nerves and is readily available.

The volume conduction method of electrical stimulation also appears to be superior to all prior suggestions for stimulating micturition, because it appears to give both more complete stimulation of the detrusor muscle; and because it does provide stimulation for certain muscles in the region in test animals such as spinal dogs, it is to be expected to likewise provide similar stimulation of the detrusor muscle and other muscles in the region in paraplegic humans.

An object of this invention is to provide for improved, controlled, micturition of the afflicted mammal by applying intermittent electrical stimulation to the motor neurons for innervating the bladder's detrusor urinae muscle of the afflicted mammal. The stimulating electrodes used as part of the control apparatus is assembled upon and securely held by a non-conductive holder and so mounted that the electrodes are a selected fixed distance apart and are caused to project a desired limited distance into the fluid in the sacral canal of the afflicted mammal. The holder, connected at one end by lead wires to an electrical source, receives an electrical signal from a selectively controllable stimulator. The electrode holder is mechanically securable to the dorsal surface of the sacral columm without the necessity of performing a complex surgical laminectomy for electrode implantation. If the dorsal surface of the sacral column has bony protrusions thereon, they may be removed to provide a substantially flat surface against which the electrode holder is to abut.

The electrodes, when properly placed and located so as to project into the body fluid within the sacral canal in the vicinity of those nerve roots that innervate the detrusor muscle of the urinary bladder, then become operatively associated with the detrusor muscle by the electric impulses conducted through the electrodes to the surrounding body fluid. These electrical impulses create an electrical field in the neighborhood of and about those nerve roots, resulting in stimulation of the nerve roots, causing contraction of the bladder's detrusor urinae muscle, and operating to create a condition that brings about substantially complete emptying of the urinary bladder. The body fluid that is in the sacral canal is not cerebrospinal fluid (CSF), which is only found inside the dura mater. Sacral spinal roots are enclosed in an extension of dura mater. The electrodes are, therefore, placed outside of epidural space enclosed by the dura mater, and will not cause leakage of cerebrospinal fluid.

BRIEF DESCRIPTION OF THE FIGURES

The invention disclosed herein will be explained in connection with Figures of drawings that aid in explaining these specifications, and wherein.

DETAILED DESCRIPTION OF THE INVENTION

Figure 1:
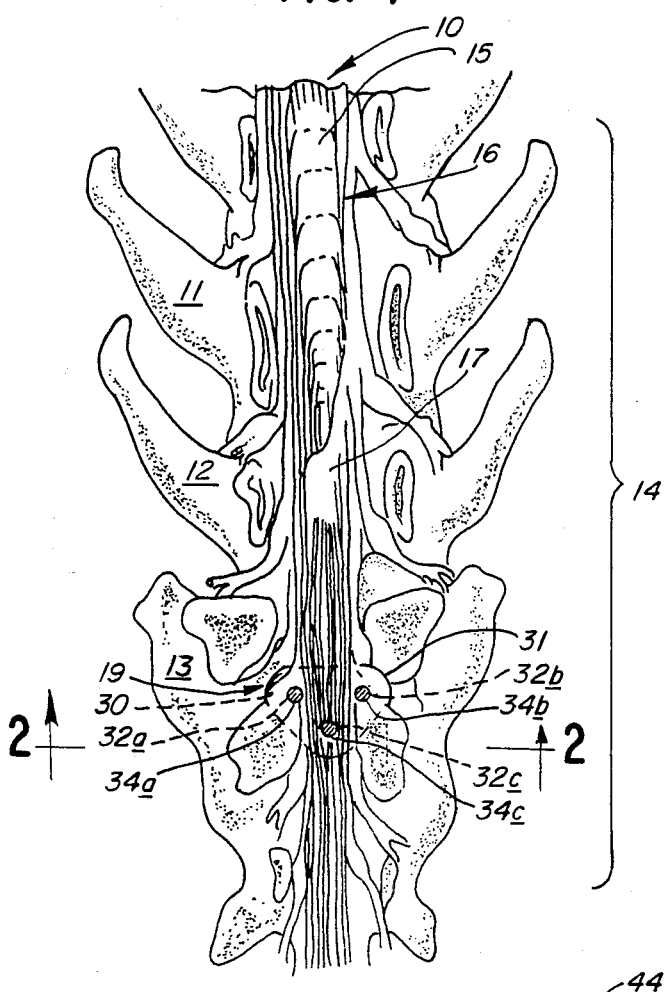
FIG. 1 is a fragmentary, illustrative view of that lowermost longitudinal portion of the portion of the spinal column that is to be involved with use of the stimulator elements and holder therefor that are herein disclosed, and said FIG. 1 also depicts, generally and not with anatomical precision, the spinal nerves in the sacral and coccygeal regions of the spinal column, the purpose of this view being to illustrate in an elevational view the location and positioning of that portion of the apparatus that is shown in FIGS. 2 and 3.
Figure 2:
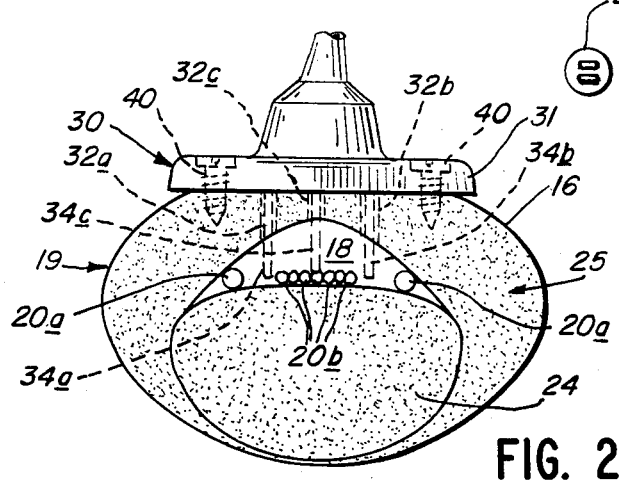
FIG. 2 is a cross-sectional view, taken substantially along the line 2—2 of FIG. 1, showing certain relevant portions of the spinal column, that includes the sacral region of a mammalian animal, specifically a dog, or a human, and upon which sacral region the stimulator assemblage of FIG. 3 is secured, and also illustrates the electrode assembly implanted in the sacral region of the spinal column, and secured to the surrounding bone by a specific, but appropriate, means.

Referring first to FIGS. 1 and 2, these FIGS. illustrate generally the region of the spinal column 10 that is involved. FIG. 1 shows the dorsal view of a lower portion of a mammal's spinal column, generally designated 10. The said lower spinal column includes bony spine structure segments commonly known as Lumbar Six, Lumbar Seven, and the Sacral vertebra, which are respectively numbered 11, 12 and 13 in FIG. 1. As seen in FIG. 1 these known bone structures, together define a longitudinally arranged spinal section 14 having therein an elongated passage, or chamber 16, or vertebral foramen. The anatomical illustrative portion of FIG. 1 is taken from page 535 of the textbook by Miller, Christensen & Evans, on *Anatomy Of The Dog*, W. B. Saunders Publishing Co. (1964).

Within this longitudinal vertebral foramen, passage, or chamber, 16 of the spinal column fragment 10 shown in FIG. 1, lies the dog's spinal cord 15. As is known, within the vertebral foramen, the spinal cord is suspended in cerebrospinal fluid which is enclosed in a sac. The wall of the sac is formed by a tough fibrous membrane, which is the fusion of the dura mater and arachnoid. The dura-arachnoid sac, shown in fragment at 17, prevents the leakage of cerebrospinal fluid. The longitudinal passage or chamber 16, formed by the structural arrangement of the bony vertebrae, becomes a laterally elongated, generally isosceles-shaped triangular space, generally indicated at 18 in FIG. 2, and located at the level of the sacrum, indicated generally at 19 in FIG. 1 and illustratively shown in cross-section as shown in FIG. 2. This space 18 is called the sacral canal. The dural sac 17 terminates at a point anterior of, or above, the level of the sacral canal as seen in FIG. 2, and the sacral canal contains ordinary body fluids which is separated from the cerebrospinal fluid by the dura mater 17. Electrodes placed in the sacral canal 18 will not cause leakage of cerbrospinal fluid as they do not puncture the dural sac. Generally similar anatomical structures, corresponding with those of a dog as shown in FIGS. 1 and 2, are found in other mammals, including humans. The chamber 16 (the vertebral foramen) of FIG. 1, and chamber 18, the sacral canal, of FIG. 2 are portions of a continuous passage. The vertebral foramen 16 contains the spinal cord. The sacral canal contains nerve roots, but no portion of the spinal cord.

The triangular space 18 of the sacral canal, as seen in FIG. 2 contain a plurality of nerve roots such as first sacral roots 20a, and sacral and coccygeal roots 20b which primarily innervate the urinary bladder. Nerve roots that innervate some other muscle portions of the body may also be present. As shown generally in FIG. 2, these nerve roots 20a and 20b are located in the sacral canal, or chamber 18, which is created by the bony vertebral structures, sacral bone 25 and the sacral body 24. Such nerve roots combine to form spinal nerves which extend through holes, or foramina in the sacrum on their way to the various parts of the body.

FIG. 2, taken generally on line 2—2 of FIG. 1, illustrates a cross-sectional view of the sacral bone 25 and sacral body 24 of the spinal column 10, at a region of a dog's anatomy that is located axially rearwardly, or posterior to, the Lumbar Seven spinal segment 12, immediately rearward of the exits of the seventh lumbar spinal nerves, as seen in FIG. 1.

At the sacral region, generally indicated in FIG. 1 at 31, and located in a dog anterior to the first sacral vertebral segment, the dural sac 17 ends and tapers into a filament, so that the dural sac fortuitously avoids being pierced by the electrodes that are implanted at a location posteriorly of said sac. As the dural sac is maintained intact, there will be no chance for leakage of cerebral spinal fluid.

At the desirable access site seen in FIG. 1, represented generally by the section line 2—2, there is shown, in phantom contour, an electrode holder 30, which is illustrated attached in place upon the bony portion of the dorsal surface of the sacrum 19. The spinal column seen in FIG. 1 includes the bony structure and the spinal cord 15 surrounded by the dura mater 17. The holder 30 is attached to the dorsal surface of the sacrum 19, and more specifically to a bone structure 25 known as the sacral arch. The body 24 seen in FIG. 2 is a posterior-located bone structure above which the spinal cord 15, enclosed in the dura mater 17, terminates. As will become apparent from the following description, the necessity of performing a surgical laminectomy, for access and implantation of the elecrode assembly 30, that is illustrated in phantom elevation in FIG. 1, has been eliminated. The electrode holder 30 is in the shape of a triangular part, as best seen in phantom in FIG. 1 and as illustrated in perspective in FIG. 3.

The holder 30 is constructed of such a size as to overlay a portion of the bony vertebral column in the sacral region 31, where the electrode assembly 30 is to be attached to the dorsal bony surface of the sacrum to effect implantation of electrodes into the sacral canal to achieve maximum desirable selective stimulation and results in effecting selectively controlled micturation, such as in a spinal dog.

Access of the electrodes of the electrode assembly to the body fluid in the sacral canal is achieved by first boring, or drilling, three passageways, or holes 32a, b and c through the dorsal bony surface of the sacrum. The length of the electrodes, 34a, 34b, and 34c, of the electrode assembly 30, is selected to be sufficient to extend through the thickness of bone 25 of the dorsal surface of sacrum and into the sacral canal, indicated as a generally triangular region 18, seen in FIG. 2, but without directly touching the nerve roots 20a, 20b. Each hole 32a, b and c has a diameter of approximately 1.2 mm. The two anterior holes 32a and 32b, that is anterior relative to the length of the body, are situated approximately 10 mm. apart and are arranged to lie between the regions of exit of the first sacral nerves 20a from the sacral canal. The distance from the location of the posterior located hole 32c, to a point that is midway between the two anterior holes 32a and 32b, is approximately 10 mm. in length.

The region shown as a generally flattened triangular area at 18 as seen in FIG. 2, is located posteriorly of the electrode assembly 30, shown in phantom in FIG. 1 and in full lines in FIG. 2. This arrangement provides that the region in which the bores, or holes, 32a, 32b, and 32c is provided, operates to properly locate the electrodes, 34a, 34b, and 34c, as seen in FIGS. 1 and 2, and that the electrodes will be properly located in the portion of chamber 16 through which the first sacral nerve roots 20a, and most of the other sacral and coccygeal nerve roots 20b, extend. The first sacral nerve roots 20a are shown in FIG. 2 separated from the group of other sacral and coccygeal nerve roots 20b. By the spacing and placement of the electrodes as shown in FIG. 2, the first sacral nerve roots 20a are intentionally spared from direct stimulation by the electrical energy introduced through electrodes 34a, 34b, and 34c, to reduce unnecessary movements of the body and the legs, which movement might cause discomfort, or even pain, in a mammal or human. Where, however, it is desired to induce movement of muscles to prevent their deterioration, it will be understood that somewhat different placement of the electrodes may be used.

Figure 3:
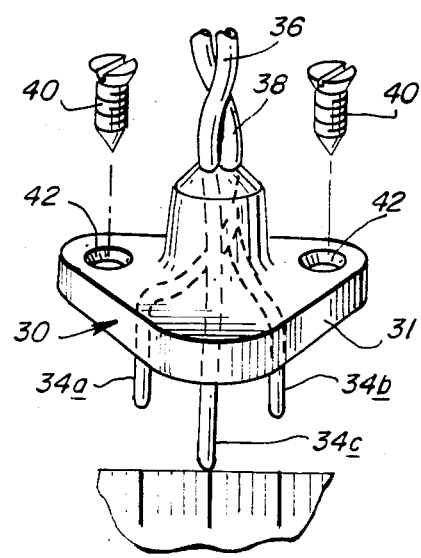
FIG. 3 is a perspective, fragmentary view of an illustrative electrode assembly designed for use, as shown in FIGS. 1 and 2, with a mammal, or human, and showing that portion of the stimulator assembly that is intended for mechanical connection to the bony portion of the body portion in the sacral region of a spinal column.

The electrode assembly 30, illustrated generally in FIG. 3, and as described hereinafter, is composed of a mounting plate, or electrode holder, generally shown at 31, that serves as a mounting for holding and accurately locating the three stimulating electrodes 34a, b and c, in a triangular configuration, having fixed spacings between the electrodes 34a, b and c, as carried by the holder 31. A pair of elongated lead wires 36, 38 are operatively associated with the electrodes 34a, 34b, 34c. An electrical receptacle (not shown in FIG. 3) is operatively associated with the other ends of the elongated lead wires 36, 38. As seen in FIG. 3, one lead wire 38 connects to both electrodes 34a and 34b, while the central electrode 34c is connected to the other lead wire 36.

The size of the electrodes 34a, b and c is illustrated by a centimeter ruler shown in FIG. 3. The electrodes 34a, b and c are made of electrically conductive, but chemically inert, metal wire, preferably 18 AWG (American Wire Gauge) platinum wire, each approximately 1.0 mm. in diameter. Each electrode 34a, b and c measures approximately 7.0 mm. in length, with approximately 1.0–2.0 mm. thereof being concealed, or non-exposed, by the bone 25 through which the electrodes 34a, b and c extend. The exact operative length of the electrodes 34a, b and c is selectable and adjustable during their implantation shown in FIG. 2. As the electrodes are electrically insulated with enamel except at the tips, this adjustability assures that the electrically conductive bare tips are in the fluid in the sacral canal and not buried in the sacral bone 25 or in the sacral body 24 of FIG. 2.

It will be understood that the illustrated arrangement and dimensions reported herein reflect an arrangement used with experimental dogs, but it is anticipated that variations may be made to adapt to usage upon humans.

Thus, and as illustrated in FIG. 3, the holder 30 has been selected to be of a generally triangular configuration. However, the holder 30 may take other shapes, for example, circular, rectangular, or T-shaped configurations without departing from the spirit of the invention.

The holder 30, carries the three stimulating electrodes 34a, b and c spaced fixed predetermined distances apart. Holder 30 is anchored to the dorsal surface of the sacral bone 25 in the sacral region that is posterior to the exits of the seventh lumbar spinal nerves. When the assembly 30 is properly implanted on a mammal animal such as a dog, the diameter sizes of the bored holes 32a, b and c and of the relatively smaller sized electrodes 34a, b and c are selected to create a close fit to preclude leakage of body fluid from the sacral canal through the holes through which the electrodes pass. If necessary, resilient means such as silicone rubber may be provided on the surface of the holder that presses against the bony structure to provide a seal that prevents leakage of fluid.

In the preferred embodiment, the holder 30 is secured to the dorsal surface of the sacrum bone 25, by a pair of diametrically located screws 40, of nonoxidizing, or non-corroding, material and with countersunk heads, inserted through countersunk through passageways 42 in the electrode holder 30. Non-corroding, or stainless steel, attachment screws or fasteners 40 are preferred, since their use for securing the holder 30 will avoid problems of corrosion which could result from reaction with chemicals in the body fluid.

The holder 30 is preferably made of a non-conductive, molded material, such as methyl-methacrylate. As in its preferred embodiment, it performs multiple functions. These functions include, but are not limited to: acting as a carrier for the fasteners 40; as a holder 30 that serves as a mounting, spacer, and insulator for the electrodes 34a, b and c, as well as acting as an insulator between the electrical current applied through leads 36, 38 and the stainless steel fasteners 40.

The two lead wires 36 and 38, preferably consist of Teflon insulated 18 AWG stranded, tinned copper wire, which are operatively connected to the electrodes. The electrical lead wire 38, connects to the two anterior, or uppermost (as seen in FIG. 3) electrodes 34a and b, serving as two equipotential electrodes, and the other electrical lead 36 connects to the posterior, or lowest, electrode 34c which is located equidistant from the two electrodes 34a and 34b.

As illustrated schematically in FIG. 4, the two lead wires 36, 38 are ultimately electrically connected through intermediate elements, later described, to an electrical connector 42 that is operatively arranged to cooperate with and receive alternating current from an alternating current outlet 44, such as a standard wall outlet that receives alternating current power. A standard wall outlet 44 provides a readily available source of sine-wave alternating current since this type of current is generally used domestically. This availability provides ready access to an electric current for a user of this invention.

DESCRIPTION OF ANIMAL TESTS

In female mongrel dogs under pentobarbital anesthesia, the spinal cord was transected at the level of the eighth or ninth thoracic vertebra. Two types of experiments were undertaken. One was to determine the effectiveness of a new method in inducing detrusor contraction and the other was to determine its effectiveness in emptying the bladder in spinal dogs. In the former experiments, the intravesical pressure was recorded through a urethral catheter at a bladder volume of 50 ml. In the latter experiments, the intravesical pressure was recorded through a uretheral catheter, at a bladder volume of 50 ml. In the latter experiments, the intravescial pressure was recorded through a ureteral catheter, leaving the urethra open to allow urine outflow. In all voiding experiments, the bladder was filled with 50 ml of saline through the ureteral catheter and in some experiments the bladder was refilled with 200 ml of saline. The urine output was collected with a funnel which was directed to flow over a drop counter. The electric output of the drop counter was integrated to roughly indicate urine flow rate. The urine was finally drained into a beaker suspended on a strain gauge which was calibrated to indicate the total volume of the urine output.

The new stimulating method consisted of placing three stimulating electrodes through the dorsal surface of the sacrum and into the sacral canal without performing laminectomy. Three holes, each approximately 1.2 mm in diameter, were drilled through the dorsal surface of the sacrum. The two anterior holes were approximately 10 mm apart and the distance from the posterior hole to the midpoint between the two anterior holes was approximately 5 mm but extended to 10 mm in later experiments. The electrode assembly was composed of an electrode holder, three stimulating electrodes, two lead wires, and an electrical receptacle. The holder was made of dental acrylic (methylmethacrylate) and the stimulating electrodes were made of 18 AWG (American Wire Gauge) platinum wire, approximately 1 mm in diameter. The exposed portion of each electrode measured approximately 7 mm in length, the exact length being adjusted during implantation. The two anterior electrodes were connected to one and the posterior electrode to the other lead wire, which was made of Teflon-insulated 18 AWG stranded, tinned copper wire. The lead wires were connected at the other ends to an electrical receptacle to receive electric current from a stimulator. The three electrodes were inserted through holes drilled through the sacral bone, and the holder was anchored to the sacrum with two stainless steel screws. This completed the entire procedure of electrode implantation.

Laminectomy was not involved in the implantation procedure. Because the dura mater tapers to a point at the implantation level, the laterally placed electrodes avoided puncturing the dura mater. The triangle formed by the three electrodes included all the coccygeal and all except the first sacral roots. During stimulation, all these roots were in the electric field of the stimulating electrodes and thus were believed to be stimulated. This method of stimulation is referred to as the "volume conduction" method of stimulation because the nerve roots were stimulated by the conduction of electric current through the fluid medium, i.e., the volume conductor.

As the method of stimulation is intended for future clinical use on humans, the form of the stimulating electric current was carefully selected to avoid nerve injury. Monophasic electric pulses, which are essentially intermittent direct currents, are known to generate gases and cause severe pH changes at the electrode terminals. The forms of stimulating current that are apparently noninjurious include capacitor-coupled pulses, biphasic pulses, and sine wave alternating currents. The voltage of capacitor-coupled pulses varied with the frequency of stimulation and the biphasic pulses are difficult to balance and expensive to use. In the tests, a 60 Hz AC was chosen as it is noninjurious to the nerve and readily available.

The results of the tests were as follows:

Intravesical pressure was recorded from 39 anesthetized spinal dogs during stimulation of sacral and coccygeal roots with the volume conduction method. Supramaximum stimulating intensity was used. The stimulating intensity that brought forth the highest intravesical pressure was considered as maximum. This was from 4 to 6 V. in all the animals tested. The stimulating intensity was made supramaximum by adding 2 V. to the maximum intensity for each animal. The supramaximum intensity was therefore from 6 to 8 V. By using this stimulating intensity, maximum contraction of the detrusor was thus assured.

During supramaximum stimulation with the volume conduction method, the intravesical pressure rose to a peak value of 95 mmHg in approximately six seconds. In all the animals tested, it took from five to ten seconds for the pressure to reach the peak. To avoid injury to the detrusor, the stimulation was turned off as soon as the pressure had reached a plateau.

With the said method of stimulation, somatic as well as autonomic fibers in the sacral and coccygeal roots were stimulated. Sharp excursions of the pressure, appearing in a tracing recording, were the result of movements mainly of the legs at the beginning and the end of stimulation.

The maximum intravesical pressures recorded from 39 female spinal dogs under anesthesia reached a high of 112 mmHg and a low of 50 mmHg, with a mean of 83.3 mmHg. In eight dogs, the peak intravesical pressures were above 100 mmHg and their body weights were 13, 19, 19, 21, 25, 27, 28 and 34 kg. In these dogs, the amplitude of the peak intravesical pressure was apparently unrelated to the body weight. In four other dogs, the peak pressures were below 60 mmHg and their body weights were 16, 18, 19, and 16 kg. In these dogs, low peak intravesical pressures appeared to be associated with low body weights.

In a few experiments, after recording of the intravesical pressure induced with the said method of stimulation had been completed, the sacrum was cut open and the sacral canal was exposed. The second and third sacral and the first coccygeal roots were suspended on bipolar electrodes and stimulated directly. The maximum intravesical pressures induced with this conventional method of stimulation were no higher than that induced with the "volume conduction" method.

In six anesthetized dogs, respiratory movements of the chest, the arterial blood pressure, the intraabdominal pressure, as well as the intravesical pressure were simultaneously recorded and displayed on a four-channel polygraph. The effects of stimulation with the present method on these physiological parameters were observed before and after spinal transection.

As an illustration, the responses from one of the six dogs are described as follows. Some erratic breathing was observed during stimulation before but not after spinal transection. Immediately following cessation of stimulation, a prolonged respiratory acceleration lasting for more than a minute ocurred both before and after spinal transection. Before spinal transection, a steep fall of arterial blood pressure accompanied by cardiac slowing occurred during and following the stimulation. After spinal transection, there was only a slight decrease in arterial pressure with no sign of cardiac slowing during and following the stimulating. Before spinal transection, the intraabdominal pressure rose sharply during stimulation. After spinal transection, it showed no change during stimulation and only a slight rise following cessation of stimulation.

Before spinal transection, the intravesical pressure increased from a resting level of 4 mmHg to a peak value of 107 mmHg, a net increase of 103 mmHg during stimulation. After spinal transection, the net increase in intravesical pressure during stimulation was 90 mmHg. However, the apparently higher increase in intravesical pressure before spinal transection was due to the sharp rise of about 13 mmHg in intraabdominal pressure during stimulation. Deducting this value from the total increase in intravesical pressure before spinal transection yields a net increase of 90 mmHg, which is identical to the increase in intravesical pressure during stimulation after spinal transection.

The responses to stimulation in other five dogs were similar.

In preliminary experiments, urine flow was not observed during stimulation but was observed following cessation of stimulation. It was hypothesized that failure of voiding during stimulation was due to contraction of the urinary sphincter simultaneously with that of the detrusor. From this hypothesis, a special stimulating procedure was introduced. It consisted of a series of brief stimulations each of which was followed by a longer resting period. Preliminary experiments showed that a stimulating period of 0.5 second and a resting period of from 3.5 to 4.5 seconds were most effective in voiding the urine from the bladder. The stimulating current was 60 Hz AC, which seems to be less likely to cause nerve damage than monophasic electric pulses. A stimulator was constructed that was capable of automatically delivering intermittent stimulations with 60 Hz AC for a duration of one minute. The stimulating and resting periods could be varied in the ranges stated above.

In 14 anesthetized spinal dogs, the 50 ml of saline that were placed in the bladder were completely voided in one minute with this stimulation procedure. In one experiment, the sacral and coccygeal roots were stimulated with a one-minute series of 12 brief stimulations of 0.5-second duration applied at 5-second intervals. The intravesical pressure rose briefly to about 60 mmHg at the onset of stimulation but there was no sign of urine outflow until cessation of stimulation. During the resting period, despite the decline of the intravesical pressure, urine continued to flow until the onset of the next stimulation. The volumes of the voided urine were approximately 8 ml, 6 ml, 10 ml, and 6 ml, respectively, following the first four consecutive stimulations. Subsequent volumes were less than 5 ml. A total of approximately 50 ml was voided from the bladder with a one-minute intermittent stimulation. As a further check, a second one-minute stimulation was applied after a resting period of five to ten minutes. In all dogs tested, resumption of stimulation yielded no urine output, indicating that the bladder had been completely emptied by the first one-minute stimulation.

As conscious spinal dogs often have large volumes of urine accumulated in their bladders, emptying the bladder containing 200 ml of saline was tested in six anesthetized spinal dogs after they had successfully voided 50 ml of saline. A single one-minute stimulation was insufficient to void this volume completely. In three dogs, two one-minute stimulations were sufficient but in the other three dogs, three one-minute stimulations were necessary to empty the bladder. In all these experiments, a resting period of five to ten minutes was allowed to follow each one-minute stimulation.

In one experiment on an anesthetized spinal dog, 143 ml of saline were evacuated from the bladder following an one-minute series of 15 single stimulations. The remaining 57 ml were voided during the second one-minute series of stimulations (FIG. 5B). In this dog, the maximum volume evacuated by a single stimulation (MSSV) was the 20 ml voided following the second single stimulation. In the other five dogs, the MSSVs were 25, 20, 20, 18 and 16 ml.

In the study on dogs, intermittent stimulations with the "volume conduction" electrodes completely emptied the bladder in anesthetized spinal dogs. As implantation of these electrodes does not involve laminectomy or puncturing of the dura mater, leakage of cerebrospinal fluid is unlikely to happen. As the stimulating electrodes are in the vicinity of or in loose contact with the spinal roots, mechanical injury of these roots is also unlikely, and the method does not appear likely to damage the nerve roots. It seems to be a promising method for future clinical use to aid para- and quadriplegics in emptying their bladders.

Figure 4:
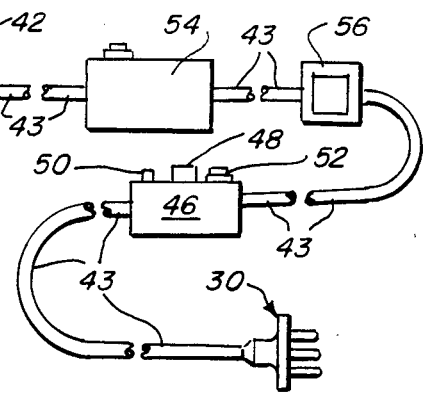
FIG. 4 is a schematic drawing of one type of apparatus that may be used by a paraplegic, for example, to permit the paraplegic to control, at will, the stimulation of his bladder's detrusor muscle to provide such an individual with control over his ability to micturate at will.

Between the electrode holder 30 and the electrical source 44, a control mechanism, such as illustrated in FIG. 4, may be provided to aid in the use of the invention. Such a control mechanism could be included in a controller box 46, shown generally as a "black box", for easy access by the user. This controller box 46 may, for example, include a manually actuatable switch, or push button 48, the depression of which, against a restoring force, operates to effect stimulation of the user's own bladder muscles, an on-off switch 50 for energizing the system, and a rotatable timer control 52, for controlling the length of the time period during which there will be provided indirect stimulation of the bladder's urinae detrusor muscles through the leads of electrode holder 30.

Additionally, to achieve maximum contraction of the detrusor muscle of the bladder, the voltage intensity to be applied may be controlled by a manually controllable step-down voltage transformer 54 between electrical source 44 and holder 30, located anywhere in the line 43 between plug 42 and holder 30. This is desirable because maximum contractions were best achieved in test animals at between 4–8 volts, and when used by humans, different voltages may be effective, but dangers of overstimulation of the bladder muscles, or of the nerve roots, innervating those muscles should be avoided, and the step-down transformer provides for selective voltage control.

The frequency of the stimulating electric current is importantly selected so as to avoid injury to a nerve or nerve root. Injury to a muscle could occur from repeated contractions, or over-stimulation of the nerve innervating that muscle. A range of frequencies from 20–60 Hz AC (alternating current) has been determined to be least injurious to nerves of test animals. It is desirable that at least 20 Hz AC and not more than 60 Hz AC be used with apparatus 30, since at this frequency, the bladder muscle or the nerves innervating the muscle have a greater liklihood of not becoming exhausted or over-stimulated. With the use of a frequency converter 56 and the step-down transformer 54, as shown in FIG. 4, which are commonly available and could easily be combined with the elements of black box 46, the desired frequency and intensity should be easily obtained, adjusted, and controlled.

When an electrode holder 30 has been properly attached to the bony structure 25 of a mammal and is operative, an electrical signal, in the form of pulses, transmitted from the electrical source 44 passes through the step-down transformer 54 to achieve the proper voltage, and through a frequency converter 56 to achieve the proper frequency before being transmitted through the manually controlled controller box 46 to the stimulating electrodes 34$a$, $b$ and $c$. This electrical pulse is applied for at least 0.1 seconds and not more than 0.5 seconds. At the end of this time period, the pulse is interrupted to allow the muscle to return to its static, or rest position. A "pulsed" electric current, such as this, continues until micturition is effected.

When a proper electric current is applied to the electrodes 34$a$, $b$, and $c$, as shown in FIGS. 1 and 2, this current is conducted from the tips of these electrodes to the surrounding fluid in the sacral canal, or chamber 16 as illustrated in FIG. 2. The fluid acts as a volume conductor that conducts the electric current to the nerve roots 20$a$ and 20$b$ in FIG. 2. As these nerve roots innervate the detrusor muscle of the bladder, their stimulation by the electric current conducted through the fluid results in contraction of the detrusor muscle, accompanied by micturition.

While the foregoing specifications disclose a number of particular improvements and arrangements for aiding micturition by mammals that are paraplegic, the inventions intended to be covered by this application will be understood, by one skilled in the art, to be limited solely by the claims appended hereto.

What is claimed and desired to be secured by Letters Patent of the United States is:

1. In a method of stimulating the detrusor muscle of the bladder of a mammal that has innervating nerve fibers operatively associated therewith, so as to effect at least partial micturition by the mammal;
   the improvement comprising the steps of:
   obtaining access to the portion of the sacral canal that is bounded by the bone of the spinal column and is not occupied by the spinal cord, said access being obtained without piercing the dura mater;

emplacing at least two electrodes through the bone of the sacrum into the sacral canal with the free ends of the electrodes immersed in the fluid in the canal but spaced form the dura mater, the spinal cord and the adjacent nerve roots;

and applying timed electrical pulsed, alternating, voltage across the electrodes immersed in the spinal fluid, to effect electrical stimulation of the adjacent nerve roots of the nerve fibers that innervate the detrusor muscle.

2. A method as in claim 1 wherein the step of emplacing electrodes includes dividing one of the two electrodes into at least two equipotential electrodes, thereby providing a total of three electrodes immersed in the spinal fluid.

3. The method of claim 1 wherein said electrical pulse is applied for a duration of at least 0.1 but less than 0.5 seconds.

4. The method of claim 1 wherein said electrical pulse is a frequency of at least 20 Hz Alternating Current but not more than 60 Hz Alternating Current.

5. The method of claim 1 wherein said electrical pulse has an intensity of at least four (4) Volts but less than 8 Volts.

6. In an apparatus for stimulating nerves in the spinal column of an animal for inducing muscle contractions of the detrusor muscle which has innervating nerve fibers operatively associated therewith, the improvement comprising, in combination:

a mounting plate for attachment to the sacral bone;

a plurality of electrical contacts split into at least two equipotential contacts, supported by said mounting plate and projecting through bores in said sacral bone into the body fluid in the sacral canal and spaced from the nerves within the spinal column associated with the sacral bone; and means holding the mounting plate in tight association with the sacral bone to prevent liquid loss from the sacral canal.

7. The apparatus of claim 6 having at least two but less than 6 electrodes.

8. The apparatus of claim 7 wherein said electrodes are of platinum.

9. The apparatus of claim 8 operatively associated with a source for supplying an electrical signal.

* * * * *